US005306242A

United States Patent [19]

[11] Patent Number: 5,306,242

[45] Date of Patent: Apr. 26, 1994

Joyce et al.

[54] RECIRCULATION THROUGH PLURAL PUMP CASSETTES FOR A SOLUTION COMPOUNDING APPARATUS

[75] Inventors: Thomas P. Joyce, Libertyville; John S. Ziegler, Arlington Heights, both of Ill.

[73] Assignee: Abbott Laboratories, Abbott Park, Ill.

[21] Appl. No.: 991,066

[22] Filed: Dec. 15, 1992

[51] Int. Cl.[5] .......... A61M 37/00

[52] U.S. Cl. .......... 604/82; 604/85; 137/563; 137/565

[58] Field of Search .......... 604/82, 83, 85, 6; 137/1, 563, 565, 3

[56] References Cited

U.S. PATENT DOCUMENTS

| | | | |
|---|---|---|---|
| 2,396,043 | 3/1946 | Evans | 604/82 |
| 2,545,445 | 3/1951 | Chatterton | 137/563 |
| 2,557,334 | 6/1951 | Zwack | 137/563 |
| 3,190,321 | 6/1965 | Robinson | 137/563 |
| 4,512,764 | 4/1985 | Wunsch | 604/80 |
| 4,625,494 | 12/1986 | Iwatschenko et al. | 53/432 |
| 5,082,014 | 1/1992 | Olichney | 137/1 |

*Primary Examiner*—C. Fred Rosenbaum
*Assistant Examiner*—Frank Wilkens
*Attorney, Agent, or Firm*—A. Nicholas Trausch

[57] ABSTRACT

An apparatus and method are disclosed for compounding of parenteral admixture solutions, and recirculation with the admixture solution being formed. The apparatus includes a multiple pump cassette configured for operative association with a pump driver, whereby one or more selected source solutions are delivered through a pump cassette to an associated admixture container. After pumping of each source solution, the present method contemplates that the admixture being formed is recirculated through the pump cassettes thereby diluting any source solution in the cassettes and associated tubing. In this manner, the possible mixture of incompatible source solutions, resulting in formation of precipitate, is desirably avoided.

13 Claims, 4 Drawing Sheets

RECIRCULATION THROUGH PLURAL PUMP CASSETTES FOR A SOLUTION COMPOUNDING APPARATUS

FIELD OF THE INVENTION

The present invention generally relates to a system for preparing patient parenteral solutions, and more particularly to a solution compounding apparatus including multiple pump cassettes and a transfer tubing set for compounding a parenteral admixture. Further the system of the present invention provides recirculation of the admixture through the cassettes and transfer tubing arrangement so as to dilute any source solution in the common fluid path and to ensure mixing of all of the dispensed source solution in the parenteral admixture.

BACKGROUND OF THE INVENTION

Currently, a large number of parenteral solutions are prepared by health care providers for intravenous or intramuscular administration to patients. Such parenteral solutions include those formulated for nutritional purposes, as well as drug-containing admixtures for therapeutic purposes. Because of the large number of such admixtures which must be prepared on a routine basis, efficient and accurate preparation of such solutions is highly desirable.

Previously, preparation of these medical solutions was performed manually by the pharmacist and assisting personnel in a health care facility. Specifically, an appropriate intravenous solution admixture container, such as a flexible patient bag, is selected, with the container typically being partially empty and containing appropriate base nutritional solutions or diluents. The pharmacist or other personnel then calculates the amounts of various liquid components that need to be added to the solution container in accordance with the physician's order. These components are then measured by drawing them into syringes of the appropriate sizes, with the contents of the syringes then injected into the final solution container.

Accurate preparation of parenteral solutions in this manner is time consuming, with the manual nature of the procedure raising the possibility of error in the preparation of the resultant admixtures. Additionally, the repeated needle-puncturing of source solution containers so as to make additions to the admixture container increases the risk of contamination as well as accidental needle stick.

Thus automatic electromechanical systems for compounding parenteral admixtures are coming into increasingly widespread use. Such systems typically include arrangements for measuring and combining one or more selected source solutions in a suitable admixture container for subsequent patient administration. Such devices ordinarily include programmable controls as well as suitable monitoring devices to greatly facilitate efficient and accurate preparation of parenteral admixtures.

The present invention relates to an admixture compounding apparatus for use in association with an automated compounding system. In particular, the present apparatus and method of use is specifically configured to dilute any mixture of potentially incompatible source solutions, which in their relatively undiluted and concentrated state could undesirably form precipitates. Also the present apparatus and method of use ensures that all dispensed source solution is mixed with the admixture in the patient container and does not remain in the common fluid path.

SUMMARY OF THE INVENTION

The present compounding apparatus and method is particularly configured to dilute mixtures of potentially incompatible source solutions and to ensure the mixing of all the dispensed source solution remaining in the common fluid path. These desirable results are achieved by recirculation of the admixture being formed in the patient container through the common fluid flow path. The recirculated admixture functions as a diluent so that formation of a precipitate by potentially incompatible source solutions is desirably avoided. Furthermore, the recirculated admixture assures that substantially all dispensed supply solution enters the patient container and that any solution remaining in the common fluid path is of the same concentration as the admixture in the patient container.

The present apparatus includes multiple pump cassettes for use in association with a like number of pump drivers of a compounding system. The pump cassettes function as a disposable interface between the source solutions to be combined and the pump driver. The whole disposable transfer set assembly is essentially a self contained arrangement and is the only part of the compounding system which contacts the various source solutions and the resultant admixture.

Each pump cassette include a plurality of liquid inlets, liquid outlets, and a liquid flow path joining the inlets and outlets in fluid communication. Each pump cassette further includes a self-contained positive displacement pump chamber for pumping liquid from a selected one of the inlets to a selected outlet. The structure of the cassette is provided by a rigid cassette body, within which an elastomeric diaphragm is positioned. The diaphragm and cassette body together define the required inlets, outlets, flow path, and liquid pump chamber. The pump cassette cooperates with the associated pump driver such that the reciprocal motion of the pump driver operates the positive displacement pump chamber. Further the cassette cooperates with the associated valve actuators to selectively open and close the various liquid inlets and outlets for fluid flow control within the pump cassette.

The present invention further includes an admixture container for receiving at least one source solution from a pump cassette for forming an admixture solution. Typically, the admixture container is a flexible patient bag such as is commonly used for preparation and administration of parenteral solutions.

The present apparatus also includes a transfer tubing arrangement for compounding the desired solution in the admixture container and diluting any source solution in the pump cassette by recirculation of the admixture solution being formed. In a particular embodiment, the arrangement includes a recirculation tubing assembly including two cassettes, first, second, and final tubing outlet conduits operatively joined by a connector, and a recirculation conduit joining the two cassettes. The first tubing outlet conduit joins the liquid outlet of the first pump cassette in fluid communication with the connector. The second tubing outlet conduit joins the respective liquid outlet of the second pump cassette in fluid communication with the connector. The final tubing outlet conduit joins the connector in fluid communication with the admixture container. The recirculation conduit joins the recirculation outlets of each cassette with the other cassette.

Compounding of liquid admixture in the patient container is produced by operating the positive displacement pump chambers of the pump cassettes to pump at least one source solution from one of the liquid inlets in the pump cassette through the liquid outlet and into the admixture container. Thus, during the dispensing step of compounding, liquid flows from the pump cassette outlet through the first tubing outlet conduit, the connector, and the final tubing outlet conduit into the admixture container.

After the desired quantity of source solution has been drawn into the system from the respective liquid inlet, the resultant admixture may be recirculated through the pump cassettes and transfer tubing set. Substantially all the source solution concentrate in the cassette and tubing system is delivered to the admixture container, with the residual admixture in the system ordinarily having a sufficiently low concentration of any individual therapeutic or nutritional so as to avoid any undesirable precipitation with a source solution subsequently introduced into the system.

The admixture is recirculated through the pump cassettes by alternately drawing the admixture from the patient container through one of the outlet tubing conduits into the respective cassette, through the recirculation conduit to the other cassette and then pumped from the other pump cassette through the other outlet tubing conduit for flow back into the admixture container. Thus, a flow path generally in the nature of a closed-loop is established so that the admixture is effectively recirculated through both pump cassettes and the associated tubing.

The admixture container is the fluid reservoir during this recirculation sequence. Diluted solution is drawn from the admixture container through one tubing outlet conduit and into the cassette flow path. Undiluted solution is not merely drawn from the first tubing outlet conduit. Accordingly, the predetermined maximum displacement volume of the positive displacement pump chamber (i.e., the volume of each pump stroke) will be greater than the volume of the final outlet conduit of the connector tubing assembly, i.e., the third branch joining the connector fluid communication with the admixture container.

Numerous other features and advantages of the present invention will become readily apparent from the following detailed description, the accompanying drawings, and the appended claims.

Figure 1:
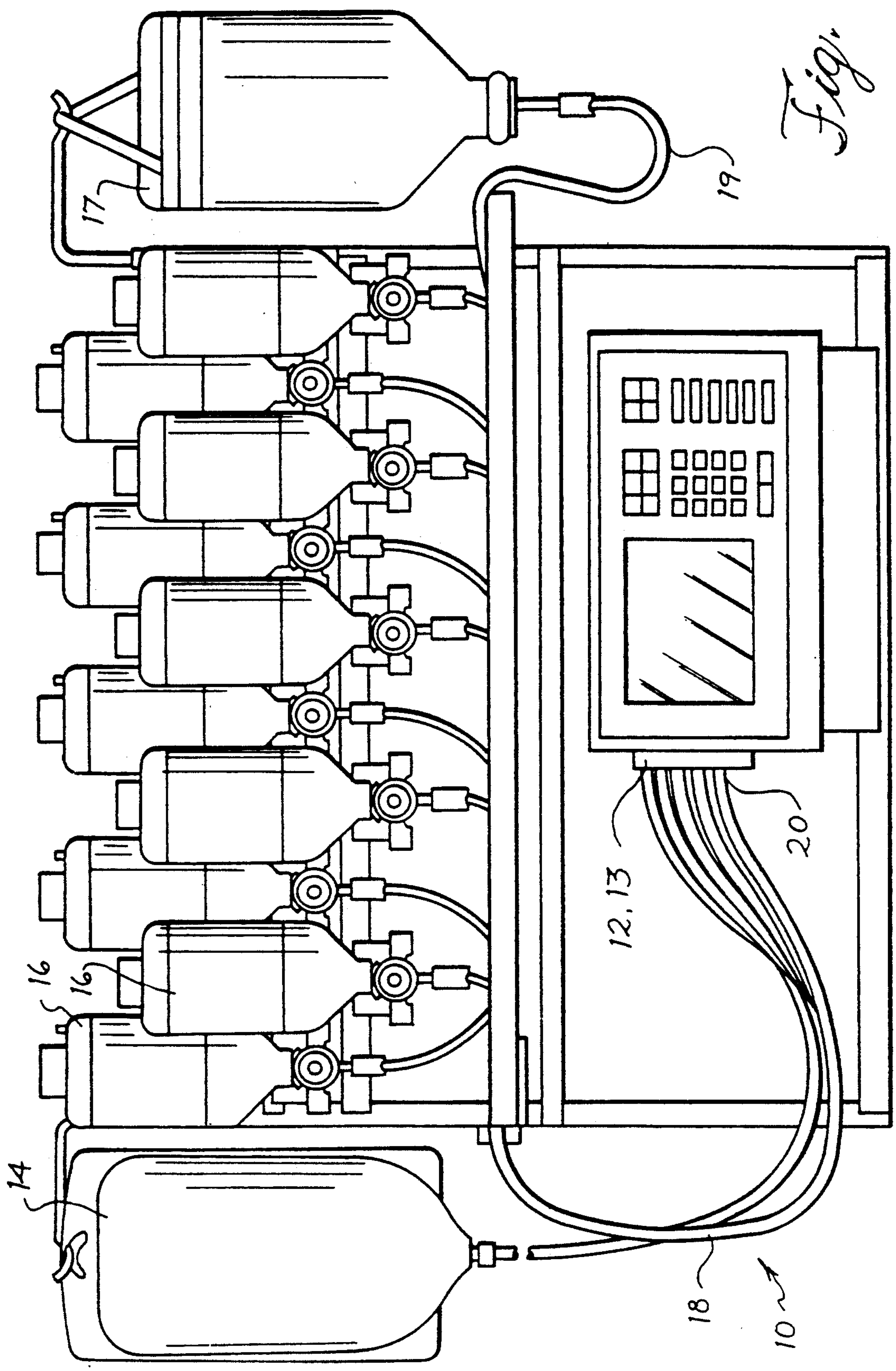
FIG. 1 is a schematic of a compounding apparatus according to the present invention.

While the present invention is susceptible of embodiment in various forms, there is shown in the drawing and will hereinafter be described a presently preferred embodiment, with the understanding that the present disclosure is to be considered as an exemplification of the invention, and is not intended to limit the invention to the specific embodiment illustrated.

DESCRIPTION OF THE PREFERRED EMBODIMENT

With reference now to FIG. 1–4, an admixture compounding apparatus 10 according to the present invention is depicted. The compounding apparatus includes two pump cassettes 12 and 13 which are configured for operation by a pair of associated pump drivers (not shown) for compounding an admixture solution in a suitable patient admixture container 14. An example of a similar embodiment of the pump cassettes 12 and 13 that are used for compounding are disclosed in greater detail in U.S. Pat. No. 5,062,774 to Kramer et al. and 5,082,014 to Olichney, both assigned to the assignee of this application and which patents are hereby incorporated by reference. As will be recognized by those familiar with the art, some features of the compounding cassettes 12 and 13 are similar to those found in the pump cassette disclosed in U.S. Pat. No. 4,818,186 to Pastrone et al., and U.S. Pat. No. 4,842,584 to Pastrone, which patents are also commonly assigned and which patents are also hereby incorporated by reference. While the disclosure of the last two cited patents particularly relates to a pump cassette and associated pump driver employed for infusion of parenteral solutions, many of the principles disclosed therein are equally applicable in connection with the present compounding apparatus.

Both pump cassettes 12 and 13 are configured for disposable use (such as on a daily basis), in the pharmacy of a health care facility, and thus includes a rigid cassette body preferably formed from suitable thermoplastic material, such as polycarbonate. In the preferred form, the cassette body includes plate-like front and rear body members which are joined together in confronting relation, with a flexible elastomeric diaphragm positioned between them. The pump cassette is preferably configured such that the front body member and the diaphragm together define the various inlets, outlet, and flow passages within the cassette. The rear body member holds the diaphragm in tightly fitting and confronting relation against the front body member. Additionally, the rear body member defines a plurality of openings which expose the flexible diaphragm within the cassette. Fluid flow within the cassette is controlled by suitable manipulation of the flexible diaphragm, through the openings in the rear body member. The diaphragm cooperates with the cassette body to provide a valve mechanism at each of the various inlets and outlets of the cassette. The diaphragm is selectively deformed and relaxed by a plurality of solenoid-operated valve actuators, and a motor-driven pump plunger of the pump driver.

The various source solutions flow through the cassettes and associated transfer tubing for compounding in admixture container 14. Each pump cassette 12 and 13 includes a plurality of source solution liquid inlets 20, respectively joined to individual source solutions 16 by individual inlet source solution tubing conduits 18. A flush solution is also joined to each cassette by flush tubing inlet conduit 19. A liquid flow path 22 and 23 joins a selected one of the liquid inlets in fluid communication with a liquid outlet 24 and 25. Liquid in the flow path flows by the operation of either one or both positive displacement liquid pump chambers 26 and 27.

The pump chambers 26 and 27 includes a chamber defined by the front body member of the cassette body and a portion of the diaphragm fitted in confronting relation with the pump chamber. The reciprocation of either or both pump plungers of the associated pump driver against the diaphragm, in timed relation with operation of a selected upstream valve mechanism (for example, one of the inlets 20), and selected downstream valve mechanism (for example, outlet 24) causes fluid flow. The timed operation of inlet and outlet valves in relation with pump chambers 26 and 27 controls liquid flow into and out of the pump cassette. It is preferred that such flow control be effected at a selected inlet and a selected outlet of the cassette in timed coordination. U.S. Pat. No. 4,639,245 to Pastrone et al., which is hereby incorporated by reference, discloses the general configuration of the positive displacement pump and associated reciprocable pump plunger. As will be appreciated, the liquid pump chambers 26 and 27 can be operated to reverse liquid flow through the pump cassette, by reversing the sequence of operation of a selected liquid inlet and a selected liquid outlet relative to the reciprocation of the pump plunger of the associated driver.

Air sensors are provided for cooperation with a suitable detector mechanism on the associated pump driver, with the sensor typically comprising a portion of the diaphragm which projects from the cassette body so that the absence of source solution, or recirculated admixture, in the flow path 22 or 23 can be automatically detected.

Each pump cassette 12 and 13 further includes a flush fluid inlet 30 and 31 joined in fluid communication with flow path 22 preferably at a terminal port. Flush inlets 30 and 31 permit introduction of flush fluid into the pump cassette for flow through the system. The transfer tubing set includes outlet conduits 32 and 34 which are connected immediately prior to the admixture container 14 by a coupler 36. A final fluid outlet conduit 38 connects the coupler with the admixture container.

Figure 2:
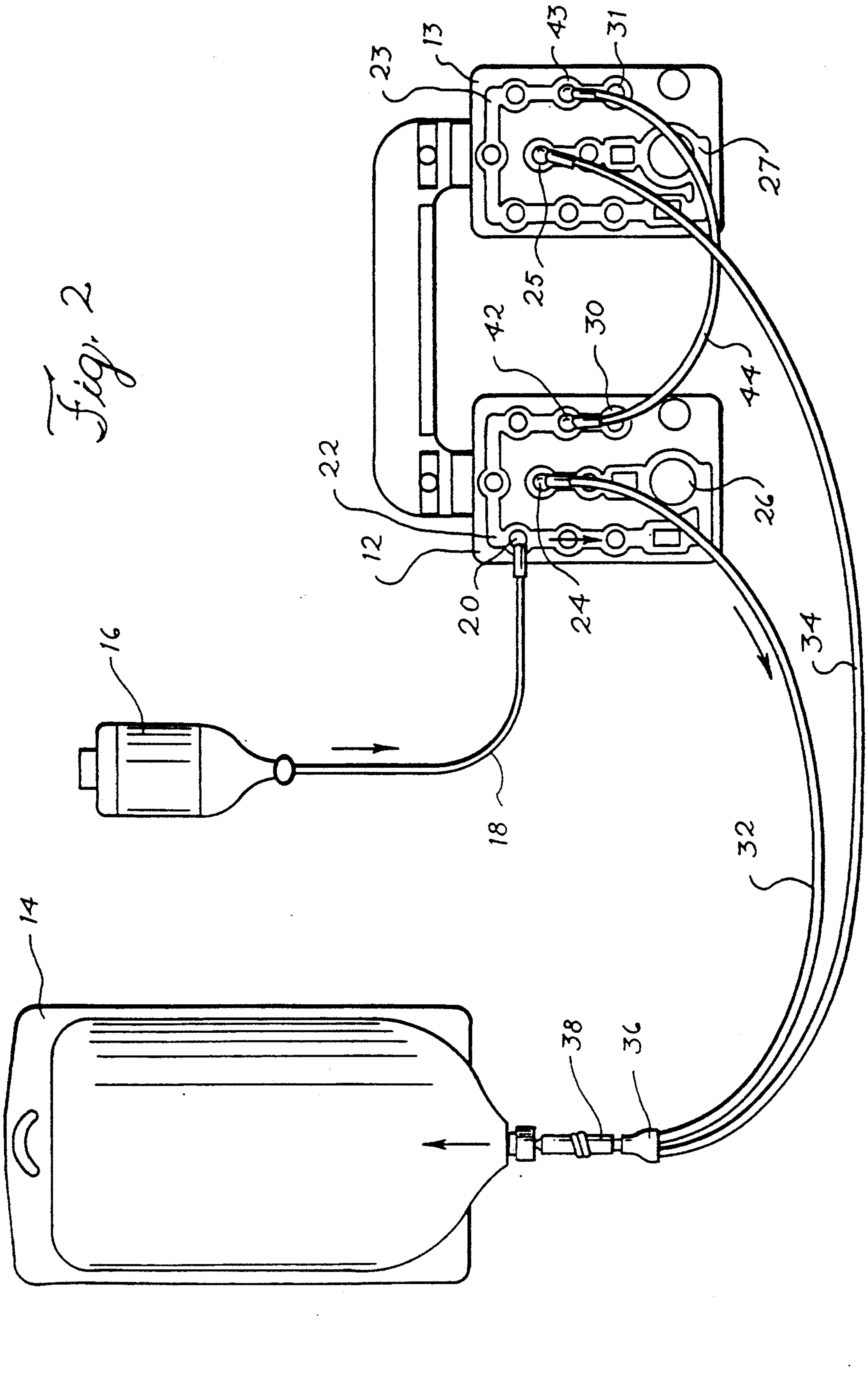
FIG. 2 is a depiction of part of an admixture compounding apparatus including a portion of a transfer tubing set and dual cassette assembly according to the present invention, showing a dispensing step.

A typical dispensing of a source solution 16 is represented in FIG. 2. Preparation of the desired admixture as prescribed by the physician is initiated by spiking a new admixture container 14 with the needle attached to the transfer tubing set. Compounding of the liquid admixture is then initiated by appropriately operating the pump chambers 26 or 27 (by operating the reciprocable pump plunger of the associated pump driver) to pump at least one source solution from one of the inlets 20 through the pump chamber 26 or 27 through the outlet 24 or 25. The solution enters the admixture container 14 through outlet tubing conduit 32 or 34 and coupler 36 and final outlet conduit 38.

Figure 3:
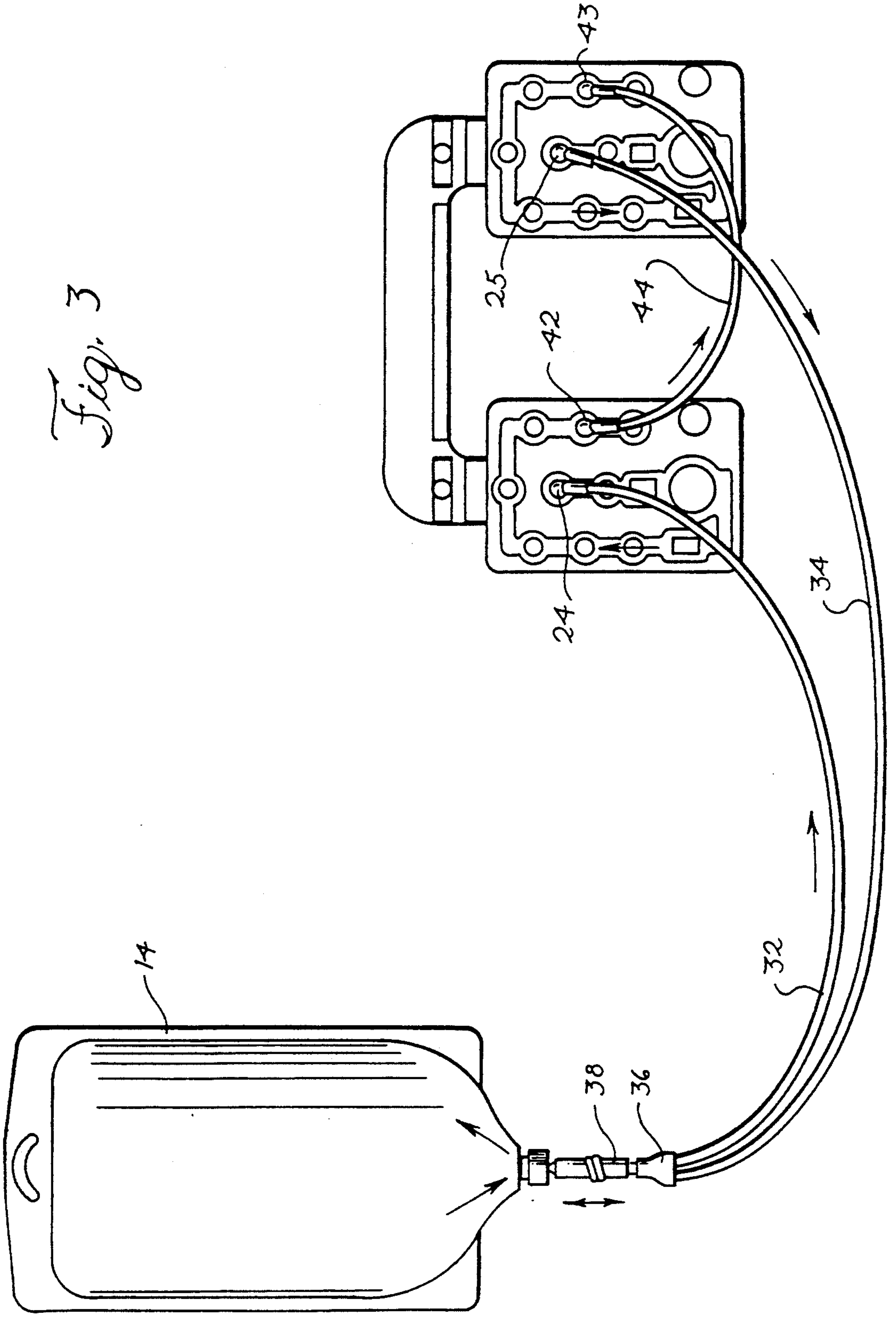
FIG. 3 is a depiction of part of an admixture compounding apparatus including a portion of a transfer tubing set and dual cassette assembly according to the present invention, showing a clockwise recirculation step.
Figure 4:
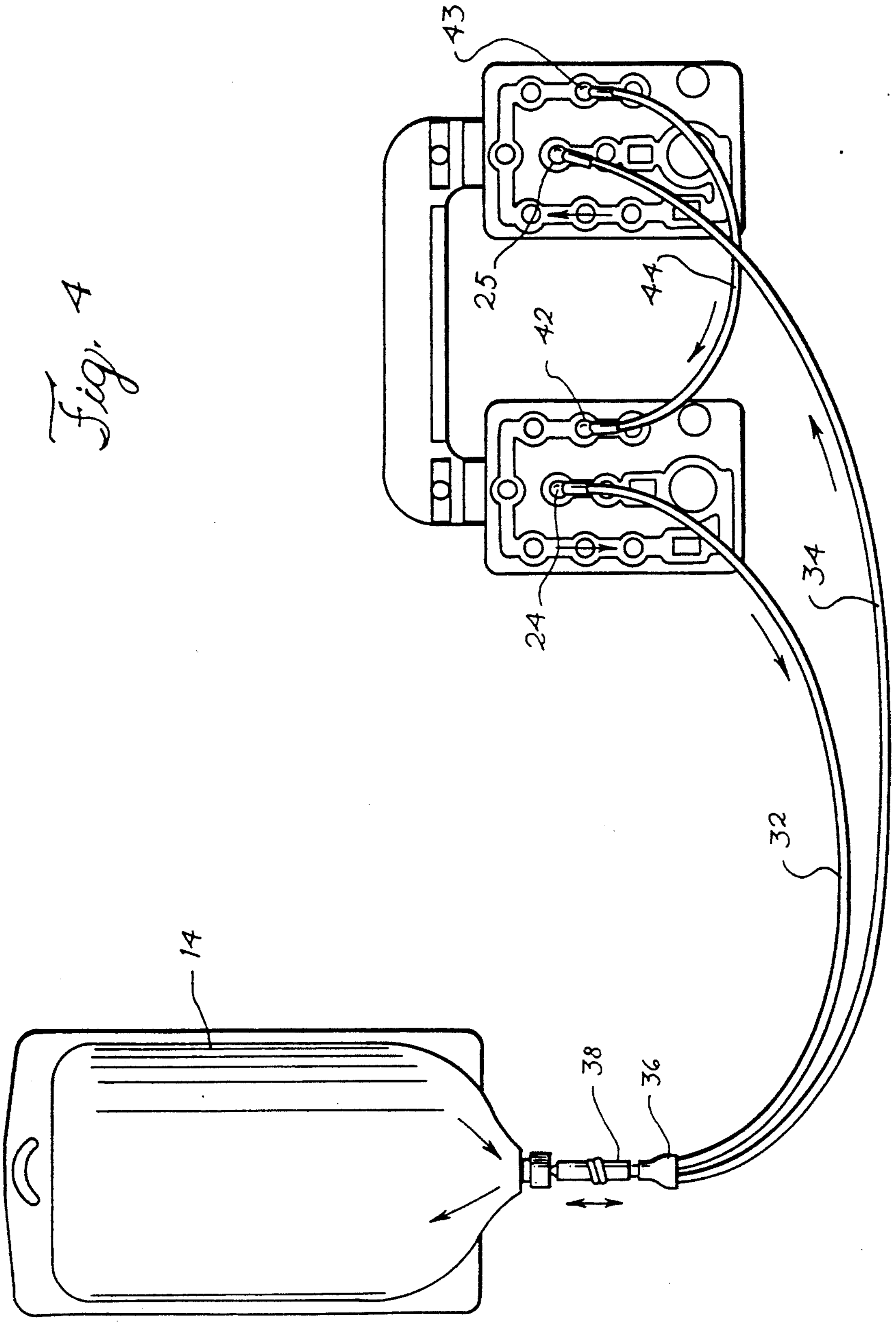
FIG. 4 is a depiction similar to FIG. 3 showing a counter clockwise recirculation step.

As shown in FIGS. 2–4, the pump cassettes 12 and 13 also include recirculation ports 42 and 43 which are positioned between the liquid inlets 20 and the fluid flush inlets 30 and 31. Inlets 42 and 43 are specifically provided to permit recirculation of the admixture solution from container 14 to dilute any undiluted source solution in the pump cassettes 12 and 13 and the transfer tubing set. When one of inlets 42 and 43 is described as providing liquid flow into the respective cassette during recirculation of the admixture, it is understood that the other "inlet" port 42 and 43 will function as an outlet port.

For recirculation of the admixture solution, the present apparatus includes a recirculation conduit 44 operatively joining liquid recirculation ports 42 and 43. The recirculation flow path includes first, second, and final tubing outlet conduits 32, 34 and 38, with the tubing conduits joined together in fluid communication by cassettes 12 and 13 and recirculation conduit 44. As illustrated in FIG. 3, first tubing outlet conduit 32 joins the liquid outlet 24 in fluid communication with the coupler 36. The second tubing outlet conduit 34 joins the outlet 25 in fluid communication with the coupler 36. Final outlet conduit 38 joins the admixture container 14 in fluid communication with the coupler 36. Recirculation conduit 44 joins recirculation ports 42 and 43.

A method for recirculation of a liquid admixture through the pump cassettes 12 and 13 will now be described with reference to FIGS. 3 and 4. When the desired quantity of one or all the source solutions has been received into the patient bag through the selected inlets 20, the respectively associated valve actuators of the pump driver is closed. After any one or after all of the source solutions has been pumped to the patient bag, recirculation according to the present invention is performed. Specifically, as shown in FIG. 3, valves 42 and 43 are opened and held open throughout the recirculation operation. Valves 24 and 25 are alternatively opened and closed in coordination with the plunger movements so as to draw admixture in through 24 and pump admixture out through 25. Alternatively, as shown in FIG. 4, the direction of flow may be reversed by reversing the actions of valves 24 and 25.

Pumping is continued for a sufficient period of time so as to recirculate the admixture being formed completely through the flow path 22 and 23 of both pump cassettes, thereby diluting any relatively undiluted source solution in the pump cassette with the admixture. Near the end of the recirculation operation, small quantities of flush solution are drawn in through 30 and 31 to flush the path between 30 and 42 and between 31 and 43. At the very end of recirculation, valves 42 and 43 are closed.

Certain volumetric relationships are required in the arrangement to ensure that admixture is drawn from container 14 for recirculation into the pump cassettes 12 and 13 through inlet 24 or 25. Specifically, the pump chambers 26 and 27 have a predetermined maximum displacement volume which is greater than the volume of the final outlet conduit 38. The final outlet conduit volume includes any interior volume of the coupler 36 which joins the conduit 38 with the first and second outlet conduits 32 and 34. This assures that admixture is drawn from the container 14 and into one of the tubing conduits 32 or 34 for eventual flow to inlet 24 or 25 during the return or filling stroke of the pump. This relationship is necessary in any embodiment of the present invention which includes a coupler and final outlet tubing assembly. Separate individual tubing connections between each of the outlets 24 and 25 and the inlets 42 and 43 to the admixture container 14 would not require the above volume relationship but would require at least four needles simultaneously piercing admixture container 14.

Compounding of the desired admixture includes operation of the pump chambers 26 and 27 and the associated source solution inlets 20 to selectively pump each of a plurality of different source solutions from respective inlets 20. To avoid the undesired mixing of incompatible source solutions, it may be necessary to recirculate the admixture after pumping each of the source solutions.

The described method flushes any undiluted source solution from the pump cassette and the associated tubing so as to prevent precipitation should an incompatible source solution be dispensed after the recirculation. The present method is also intended to transfer the majority of the selected source solution that is in the tubing assembly into the admixture container 14. Alternatively, admixture recirculation is also performed at the conclusion of the admixture preparation to ensure that the last-selected source solution is transferred to the admixture container and not left in the associated tubing.

Recirculation may be followed by flushing of the pump cassettes 12 and 13 with flush fluid, such as sterile water. This flush fluid is introduced into the cassette through inlet 30 or 31, and is intended to push any remaining admixture out of the final outlet tubing assembly 38 and into the admixture container 14. The use of sterile water or other suitable neutral solution is desired since only a small amount of the sterile water is introduced into the admixture container 14.

Flushing is performed by dispensing from inlets 30 and 31 as if they were source solutions. The recirculation conduit 44 is flushed by opening ports 42 and 43 and pumping flush fluid in through port 31 to port 43 and out through port 42.

For flushing of the first tubing outlet conduit 32, pump 26 can be operated to alternately draw flush fluid in through inlet 30, and to pump the flush fluid out through outlet 24 and into first tubing outlet conduit 32. Specifically, inlet 42 is closed, and with pump outlet valve 24 open, flush fluid inlet 30 and outlet 24 are alternately opened and closed in synchronization with stroking of the pump 26 by the associated reciprocable pump plunger. Tubing outlet conduit 34 can be flushed in a similar manner.

Numerous modification and variations can be effected without departing from the true spirit and scope of the present invention. It is to be understood that no limitation with respect to the specific embodiment illustrated herein is intended or should be inferred. The disclosure is intended to cover by the appended claims all such modifications as fall within the scope of the claims.

What is claimed is:

1. An apparatus for compounding an admixture solution from at least one source solution, comprising:

first and second pump cassettes, each cassette having a fluid flow path including a plurality of liquid inlets and liquid outlets, the liquid flow path joining said inlets and said outlets in fluid communication, and positive displacement pump means for pumping liquid from a selected one of said inlets through a selected one of said outlets;

an admixture container for receiving at least one source solution from one of said first and second pump cassettes for forming an admixture solution; and recirculation means comprising means for joining an outlet of the first cassette with an inlet of the second cassette, and the outlet of the second cassette with the admixture container, and the admixture container with the inlet of the first cassette, whereby said first and second pump cassettes are operable to alternately draw said admixture from said admixture container and into said recirculation means for flow into the inlet and pump liquid from the pump cassettes through said recirculation means for flow into said admixture container.

2. The apparatus for compounding an admixture in accordance with claim 1, wherein said recirculation means includes first, second, and final tubing conduits, said first tubing conduit joining said liquid outlet in fluid communication with said second and third tubing conduit, said second tubing outlet conduit joining said one liquid inlet in fluid communication with said first and third tubing conduits, and said final tubing conduit joining said admixture container in fluid communication with said first and second tubing outlet conduits.

3. The apparatus for compounding an admixture in accordance with claim 2, wherein said positive displacement pump means has a predetermined maximum displacement volume which is greater than the volume of said final tubing outlet conduit.

4. A method of compounding a liquid admixture using at least two pump cassettes, each pump cassette have a plurality of liquid inlets joined in fluid communication with a liquid outlet through a liquid flow path, and at least two positive displacement pump means for pumping liquid from a selected one of said inlets to said outlet, said method comprising the steps of:

providing an admixture container;

providing liquid tubing means for joining said liquid outlet and an upstreammost one of said liquid inlets in fluid communication with said admixture container;

compounding a liquid admixture in said admixture container by operating each of said at least two pump means to pump at least one source solution from a downstream one of said liquid inlets through said liquid outlet and into said admixture container; and recirculating said liquid admixture through said at least two pump cassettes.

5. The compounding method in accordance with claim 4, wherein said recirculating step comprises:

alternately drawing said admixture from said container through said tubing means for flow into said upstream most liquid inlet; and pumping liquid from said at least two pump cassettes through said tubing means for flow into said admixture container.

6. The compounding method in accordance with claim 5, wherein said liquid tubing means comprises a Y-set tubing assembly including first, second, and third tubing conduits, said first tubing conduit joining said liquid outlet in fluid communication with said second and third tubing conduits, said second tubing conduit joining said upstreammost liquid inlet in fluid communication with said first and third tubing conduit, and said third tubing conduit joining said admixture container in fluid communication with said first and second tubing conduits.

7. The compounding method in accordance with claim 6, wherein each of said at least two positive displacement pump means has a predetermined maximum displacement volume, said maximum displacement volume being greater than the volume of said third conduit of said Y-set tubing assembly.

8. The compounding method in accordance with claim 4, wherein said compounding step includes operating each of said at least two pump means to selectively pump each of a plurality of source solutions from respective downstream ones of said liquid inlets, and said recirculating step includes recirculating the liquid admixture being formed through each of said at least two pump cassette after pumping of each of said source solutions.

9. The compounding method in accordance with claim 4, including flushing said pump cassette with a flush fluid introduced into a fluid inlet disposed in fluid communication with said liquid flow path downstream of said liquid outlet, and reversibly operating said positive displacement pump means so that said flush fluid flows through said flow path and out of said upstream-most inlet.

10. A fluid pumping apparatus and transfer tubing set for transferring fluids from multiple supply containers to a single receiving container, the pumping apparatus and transfer tubing set comprising:

two pumping components, each pumping component having a fluid flow path through the component;

a plurality of fluid ports in each fluid flow path of the two pumping components including a fluid outlet port at one end of the flow path, a flush fluid inlet port at the other end of the flow path, and at least one supply fluid inlet port and a fluid recirculation port positioned between said fluid outlet port and said flush fluid inlet port;

a plurality of fluid inlet conduits, each inlet conduit connecting one of said multiple supply containers to one of said at least one supply fluid inlet port in each of said two pumping components;

two fluid outlet conduits, each outlet conduit connected to a fluid outlet port in each of said two pumping components;

means for fluidly coupling the two fluid outlet conduits immediately upstream of the receiving container;

a fluid recirculation conduit connecting said fluid recirculation port of one of said two pumping components with the fluid recirculation port of the other of said two pumping components so as to allow fluid flow through the fluid recirculation conduit in selectively alternate directions; and a final fluid outlet conduit fluidly connecting the coupling means with the receiving container.

11. The fluid pumping apparatus and transfer tubing set of claim 10 wherein said two pumping components are two pumping diaphragm cassettes each having a pumping chamber in the fluid flow path.

12. The fluid pumping apparatus and transfer tubing set of claim 11 wherein the final fluid outlet conduit has a fluid volume less than the fluid volume of each pumping chamber.

13. The fluid pumping apparatus and transfer tubing set of claim 12 wherein the two pumping diaphragm cassettes are fluidly connected by the coupling means so as to allow fluid recirculation from the receiving container sequentially though the fluid flow path of each pumping diaphragm cassette.

* * * * *